`US006554982B1`

United States Patent
Shin et al.

(10) Patent No.: US 6,554,982 B1
(45) Date of Patent: Apr. 29, 2003

(54) MINIATURIZED SOLID-STATE REFERENCE ELECTRODE WITH SELF-DIAGNOSTIC FUNCTION

(75) Inventors: Jae Ho Shin, Seoul (KR); Sung Dong Lee, Kyungsangbuk-do (KR); Hakhyun Nam, Seoul (KR); Geun Sig Cha, Seoul (KR); Byeong Woo Bae, Kyunggi-do (KR)

(73) Assignee: Infopia Co., Ltd. (KR)

( * ) Notice: Subject to any disclaimer, the term of this patent is extended or adjusted under 35 U.S.C. 154(b) by 0 days.

(21) Appl. No.: 09/889,032

(22) PCT Filed: Mar. 24, 2000

(86) PCT No.: PCT/KR00/00261
§ 371 (c)(1),
(2), (4) Date: Jul. 12, 2001

(87) PCT Pub. No.: WO00/58720
PCT Pub. Date: Oct. 5, 2000

(30) Foreign Application Priority Data

Mar. 25, 1999 (KR) .............................................. 99-10210

(51) Int. Cl.⁷ ...................... G01N 27/401; G01N 27/333
(52) U.S. Cl. ....................... 204/401; 204/412; 204/414; 204/435
(58) Field of Search ................................ 204/435, 414, 204/401, 412

(56) References Cited

U.S. PATENT DOCUMENTS

| | | | |
|---|---|---|---|
| 4,112,352 A | * | 9/1978 | Barben |
| 4,116,798 A | * | 9/1978 | Magar et al. |
| 4,235,689 A | | 11/1980 | Petersen et al. |
| 5,230,786 A | * | 7/1993 | Preidel |
| 5,308,468 A | | 5/1994 | Katoh et al. |

FOREIGN PATENT DOCUMENTS

| | | |
|---|---|---|
| DE | 40 09 746 A1 | 10/1991 |
| EP | 0 539 912 A2 | 10/1992 |
| EP | 0 539 912 A3 | 10/1992 |
| JP | 04065666 | 3/1992 |

OTHER PUBLICATIONS

Cranny, A.W.J., et al., "Thick Film Silver–Silver Chloride Reference Electrodes", Meas. Sci. Technol. 9, pp. 1557–1565 (1998). Month unavailable.
Nagy K., et al., "Promising New Solid–State Reference Electrode", J. Electrochem. Soc., vol. 144, No. 1, pp. L1–L2 (Jan. 1997).
Nolan, M., et al., "Fabrication and Characterization of a Solid State Reference Electrode for Electroanalysis of Natural Waters with Ultramicroelectrodes", Anal. Chem., vol. 69, No. 6, pp. 1244–1247 (Mar. 1997).
Potter, W., et al., "Miniaturized Reference Electrode Based on a Perchlorate–Selective Field Effect Transistor", Anal. Chem, vol. 67, No. 24, pp. 4586–4588 (Dec. 1995).

* cited by examiner

Primary Examiner—T. Tung
(74) Attorney, Agent, or Firm—Muserlian, Lucas & Mercanti, LLP

(57) ABSTRACT

The present invention relates to a reference electrode for a potentiometric electrode system, characterized in that the junction in contact with a sample solution is enlarged and an ion-sensitive membrane containing an ion selective material as a protective membrane for the inner reference solution is employed, which comprises a substrate; a metal layer; an insoluble metal salt layer; an insulating film for insulating the metal layer from an aqueous solution; a hydrogel serving as an inner reference solution; the junction on the hydrogel contacting with a sample solution; the ion-sensitive, protective membrane formed over all surface areas of the hydrogel, except for the junction, to separate the sample solution from the inner reference solution or act as an ion-sensing membrane upon the contamination of the junction, whereby the operational abnormality caused by junction contamination may be easily checked and fast activation may be achieved.

17 Claims, 8 Drawing Sheets

MINIATURIZED SOLID-STATE REFERENCE ELECTRODE WITH SELF-DIAGNOSTIC FUNCTION

TECHNICAL FIELD

The present invention relates to a solid-state reference electrode for a potentiometric electrode system and, more particularly, to a miniaturized solid-state reference electrode characterized by employing an ion-sensitive membrane containing an ion-selective material as protective membrane for its inner reference solution and enlarging area of junction contacting with the sample solution, whereby operational abnormality may be checked by itself and fast activation may be achieved.

PRIOR ART

The levels of molecules of interest in liquid are useful indexes with which the liquid states can be perceived and thus, it is very important to quickly and accurately measure the molecular levels in physiological fluids such as blood, urine and the like, for the purpose of clinical analysis. Such importance is also true of domestic water, such as tap water and sewage, and industrial water and wastewater in environmental and health aspects. In addition, industrial final products, by-products, and intermediates are necessary to be analyzed as particular molecules in order to check the product quality.

Electrode systems utilizing potentiometry find numerous applications for the analysis of a broad spectrum of molecules ranging from biochemical compounds such as urea, creatinine, glucose in blood and urine to ions such as $K^+$, $Na^+$, $NH_4^+$, $Ca^{2+}$, $Mg^{2+}$, $HPO_4^{2-}$, $Cl^-$, $CO_3^{2-}$, etc., and gases, such as pH, $pCO_2$, $pC_2$, $pNO_x$, $pSO_x$, etc. in industrial materials for the clinical analysis, water examination, and technical analysis fields.

Generally, such a potentiometric electrode system consists of two electrodes: a working electrode that reacts with an interested ion to generate a potential difference; and a reference electrode that maintains a predetermined potential. In this system, the potential values measured on the working electrode are not absolute, but they show the relative values to the predetermined potential maintained by the reference electrode, in other words the potential difference between the working electrode and the reference electrode. Therefore, the development of a stable reference electrode to maintain a predetermined potential has a very great significance in the advance o the potentiometric electrode system.

The potentiometry for the analysis of clinical, liquid and industrial materials, like other assay methods, requires the samples to be unchanged after they are taken. However, the samples are likely to be contaminated during transportation or changed in quality owing to a measurement delay, resulting in inaccuracy. Thus, such analysis requires point-of-care for measurement. In particular, medical assay for clinical materials, such as blood, must solve the above problems as well as rarity of the samples because only a small amount of biomaterials from a testee, for example, a medical patient, is allowed for clinical purposes.

To meet these requirements, active research has been and continues to be directed to the miniaturization of measuring apparatuses. In this regard, an essential prerequisite is to micronize the electrode system consisting of working electrodes and reference electrodes. In fact, it is not too much to say that it is essential for the miniaturization of potentiometric electrode systems. Of the components of the potentiometric electrode system, the working electrode has been and continues to be under active research and, as a result, many methods are realized and suggested. On the other hand, the micronization of the reference electrode which is the counterpart of the working electrode seems to be very far away from success and actually, has been under scanty study and leads to the greatest obstructive factor to achieve the miniaturization of the entire potentiometric electrode system.

As reference electrodes, calomel Ag/AgCl electrodes are conventionally used while a capillary tube or a porous ceramic functions as a junction therein. However, these conventional reference electrodes are impossible to be miniaturized and manufactured on a large scale. In addition, the conventional reference electrodes suffer from high production cost. As a result, they are not suitable for the application for small or disposable analyzers.

Various attempts have been made to develop solid-state reference electrodes sufficient enough to be applied for small potentiometric electrode systems and the following two techniques have been evaluated as the most successful.

One technique is to employ liquid junctions, instead of solid junctions, such as conventional capillary tubes or porous materials, in which two flow systems are constructed: one flow system for an electrode of an insoluble metal salt, such as AgCl, the other for a working electrode. These two flow systems are designed to meet at a point at which an electrode junction is formed. Electrodes of insoluble metal salts are reactive to particular ions (AgCl to Cl ions). Flowing a reference solution comprising the particular ions (in case of AgCl, NaCl solution) with constant concentration to the flow system have the insoluble metal salt electrode kept as a constant potential (reference electrode system). On the other hand, when calibrants or sample solutions have flowed through the flow system in which a working electrode is established, the working electrode reacts with the particular ion and a potential change is measured as the potential difference relative to the reference electrode system. The mentioned reference electrode, even if it is relatively simple in the construction, suffers from the disadvantages of requiring an additional reference solution and being high in maintenance cost, further the flow may not be easily controlled because of its solution flow division into two.

The other alternative provides a structure in which a reference solution is formed into a hydrogel on an insoluble metal salt such as AgCl and a polymer protective membrane is coated over all areas of the hydrogel, except for a window (junction) at which the hydrogel make contact with a sample solution. Saturation of the inner reference solution with a salt such as KCl makes the potential of the insoluble metal salt constant, but the saturated salt gradually comes out through the junction, changing the salt concentration of the hydrogel and thus, the potential of the insoluble metal salt electrode. Further, the insoluble metal salt electrode plays a role as a reference electrode for several minutes before the occurrence of a potential change. This type of a reference electrode enjoys advantages of being easy to construct and control, therefore, no additional constructions are required. However, this conventional reference electrode has some problems in that the activation time of hydrogel for the normal operation, that is, the time for the hydrogel to absorb moisture from the sample for maintaining the stabilization, is relatively long. Further, the small window that serves as a junction is apt to be constructively inaccurate or is frequently clogged by impurities such as floating materials of samples. Moreover, the abnormality of the reference electrode caused by the above problems cannot be detected without operating the reference electrode, so that the measured values are poor in reliability.

DISCLOSURE OF THE INVENTION

The intensive research on potentiometric electrode systems have been repeated to overcome the above problems of conventional reference electrodes, resulting in the discovery of the employment of an ion-selective material into the protective membrane of the inner reference solution, together with an enlarged reference electrode junction in contact with a sample solution, enables the determination as to whether the reference electrode is under operational disorder such as contamination as well as reduction of the contamination at the junction and guarantees the reference electrode to be fast activated in a solution.

Therefore, it is an object of the present invention to provide a solid-state reference electrode with a self-diagnostic function, which is improved in junction contamination and can be activated within a short period of time.

According to the present invention, there is provided a planar-type solid-state reference electrode comprising a substrate; a metal layer; an insoluble metal salt layer; an insulating film for insulating the metal layer from an aqueous solution; a hydrogel serving as an inner reference solution; an enlarged junction on the hydrogel, at which the hydrogel is in contact with a sample solution; an ion-sensitive, protective membrane formed over all surface areas of the hydrogel, except for the junction, to separate the inner reference solution from the outer sample solution and act as an ion-sensing membrane upon the contamination of the junction.

BRIEF DESCRIPTION OF THE DRAWINGS

The above and other objects, features and other advantages of the present invention will be more clearly understood from the following detailed description taken in conjunction with the accompanying drawings, in which.

BEST MODES FOR CARRYING OUT THE INVENTION

Figure 1:
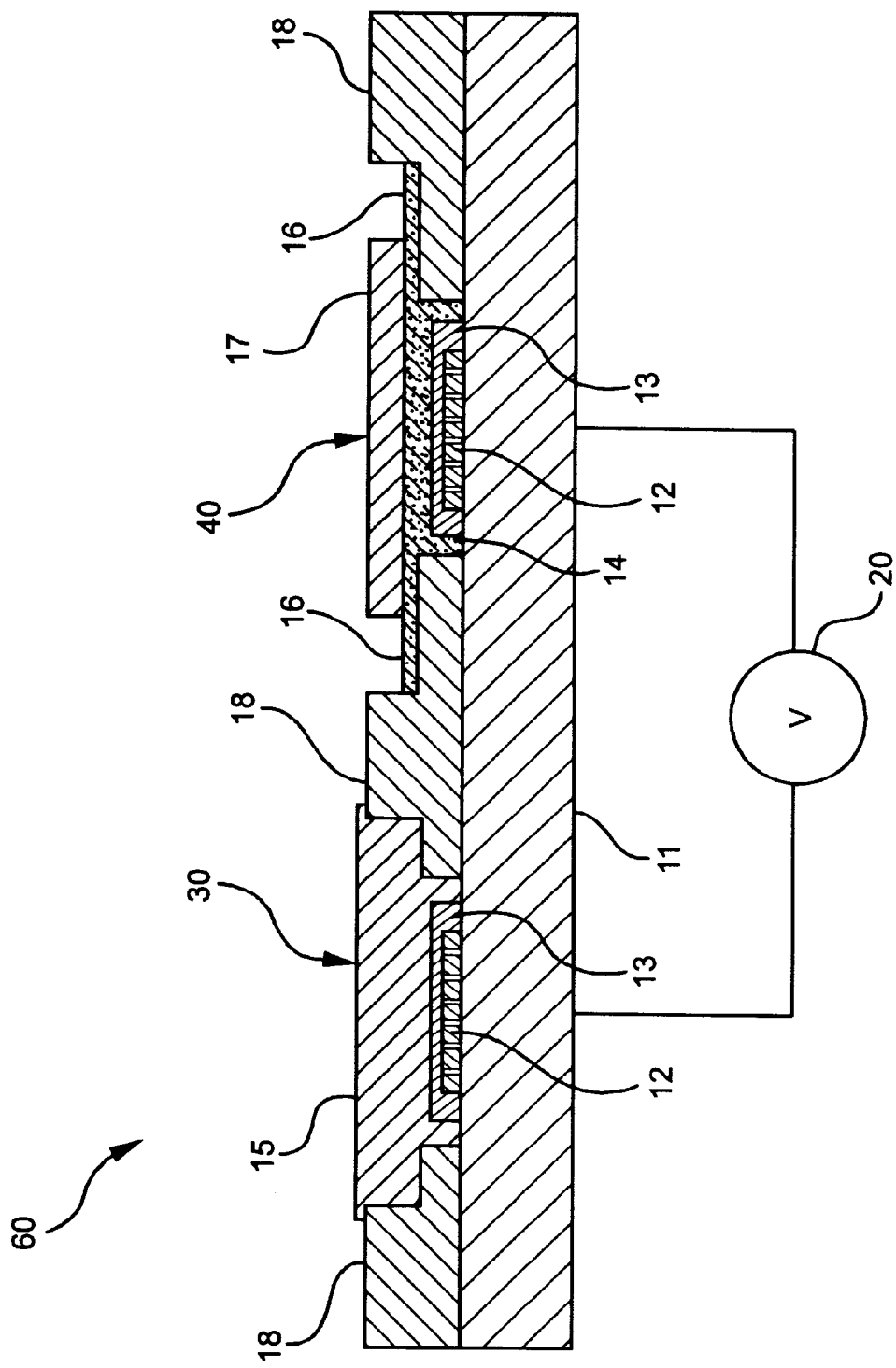
FIG. 1 is a schematic cross sectional view showing a potentiometric bi-electrode system consisting of a working electrode and a reference electrode.

The present invention provides a solid-state reference electrode for potentiometric electrode systems, characterized by the enlarged junction contacting with a sample solution and an ion-sensitive membrane containing an ion selective material as a protective membrane for the inner reference solution.

The planar solid-state reference electrode according to the present invention has such a self-diagnostic function that its operational abnormality can be autogenously detected, thereby improving the reliability of measured values. Further, error occurrence due to junction contamination is reduced and a short period of time for its activation in a solution is easily achieved with the enlarged junction area.

The present invention provides a planar-type solid-state reference electrode comprising a substrate 11, a metal layer 12, an insoluble metal salt layer 13, an insulating film 18, a hydrogel 14 serving as an inner reference solution, two or more junctions or junction sites 16 formed on and by the hydrogel 14 and adapted to be in contact with a sample solution 60, and an ion-sensitive, protective membrane 17 formed over all surface areas of the hydrogel 14, except for the junctions 16. The ion-sensitive, protective membrane 17 functions to separate the inner reference solution (the hydrogel 14) from the outer sample solution 60 and acts as an ion-sensing membrane upon the contamination of the junctions 16.

An ion-sensing membrane (ion-sensitive membrane) containing an ion-selective material into a simple polymer membrane such as polylvinyl chloride), polytetrafluoroethylene, silicone rubber, polyurethane, etc., is used as a protective membrane for the hydrogel. When the junction is not contaminated, the ion-sensitive membrane serves just as a protective membrane that separates the sample solution from the inner reference solution (hydrogel). In this case, the ion-sensitive membrane makes an open circuit so that it is excluded from the components of the circuit for the electrode system. On the other hand, the contamination of the junction makes the circuit close thus, the ion-sensitive membrane acts as an intrinsic sensing membrane and shows characteristic responses. Accordingly, the operational features according to the contamination at the junction of the reference electrode employing the ion-sensitive, protective membrane may have the reference electrode diagnosed as being normal or abnormal, that is, as to whether the junction is contaminated or not during the calibration of the electrode system before the sample test.

While the conventional techniques in which the junction is formed at only one site of the reference electrode, the present invention is characterized in that at least two sites of the reference electrode are provided as the separate junction. Accordingly, although the reference electrode of the present invention has one junction site contaminated, the electrode can be performed with the other junction. In addition, the reference electrode of the present invention absorbs moisture through two or more junction sites, so that the reference electrode according to the present invention can reach the activation within a shorter period of time than the conventional reference electrode with only one junction site.

Figure 2:
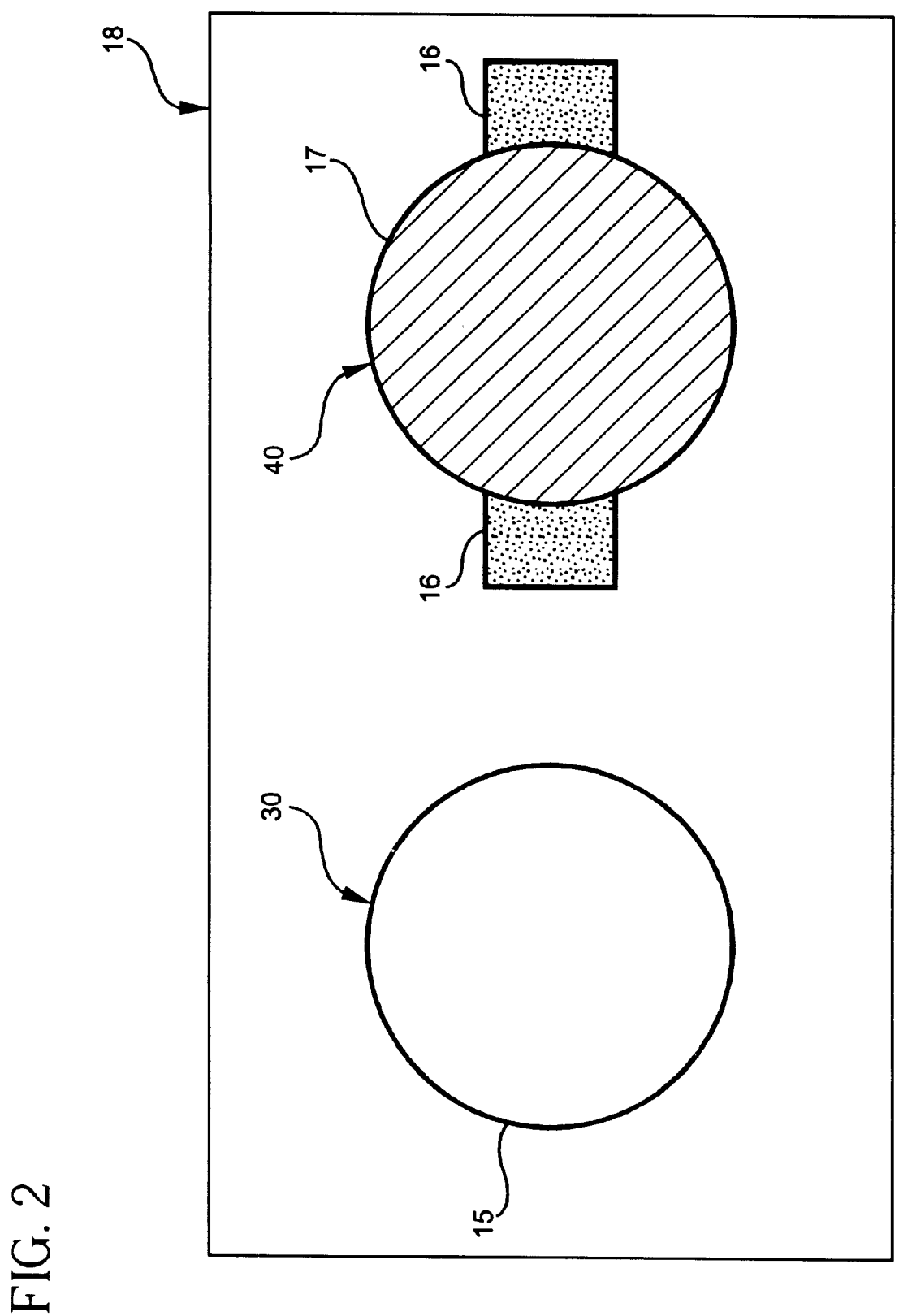
FIG. 2 is a front view of the potentiometric bi-electrode system of FIG. 1.

A potentiometric bi-electrode system according to the present invention is shown in FIGS. 1 and 2, comprising a working electrode 30, a reference electrode 40, and a voltmeter 20 for measuring the potential difference between the two electrodes.

In detail, the working electrode 30 comprises a substrate 11, a metal layer 12, an insoluble metal salt layer 13, an insulating film 18, and an ion-selective electrode membrane 15. The substrate 11 is made of plastic such as poly(vinyl chloride) or ceramic such as alumina ($Al_2O_3$). A metal for the metal layer 12 is selected from the group consisting of silver (Ag), platinum (Pt), gold (Au), copper (Cu) and alloys thereof. The insoluble metal salt layer 13 is formed chemically or physically on the metal layer 12. As for the insoluble metal salt, it is preferably selected from the silver halide group consisting of silver chloride (AgCl), silver bromide (AgBr), and silver iodide (AgI). Serving to insulate the metal layer from the solution used in the electrode system, the insulating film 18 is exemplified by a dielectric film. The ion-selective electrode membrane 15 reacts with an ion of interest.

The reference electrode 40 includes a substrate 11, a metal layer 12, an insoluble metal salt layer 13, and an insulating film 18 as the working electrode 30, and further includes a hydrogel 14 as an inner reference solution. Furthermore, the reference electrode 40 in accordance with the present invention comprises an ion-sensitive, protective membrane 17 over all areas of the hydrogel 14, except for at least two junctions or junctions sites 16 formed by the hydrogel 14, which acts to separate a sample solution 60 from the inner reference solution 14 as well as playing a role as an ion-sensing membrane upon the contamination of the junctions 16. The metal layer 12 and the insoluble metal salt layer 13 are made of the same materials as the comparable elements in the working electrode. The hydrogel 14 is prepared by dissolving a water-soluble compound selected from the group consisting of polyacrylic acid, METHOCEL® (methylated celloluse or methylcellulose), polyvinylalcohol, (hydroxypropyl)methyl cellulose, polyvinylpyrrolidone, poly(methyl methacrylate), agar and gelatin at 0.5–30 wt % in a saturated solution of KCl, $KNO_3$, or $NH_4NO_3$ in water. As the ion-sensitive, protective membrane 17, a usual ion-selective electrode membrane may be adopted, which is exemplified by a potassium ion-, a sodium ion-, a calcium ion- and a chloride ion-selective electrode membrane. Silicone rubber or polyurethane may also be used as a polymer support for the ion-sensitive, protective membrane.

Also, the present invention is featured in that a collection electrode is further employed for more accurate self-diagnostic function, in addition to the above organization.

Superior as it is in the self-diagnostic function, activation time, and potential stability, the potentiometric bi-electrode system of the present invention is limited to the condition that the reliability of the reference electrode is linked with that of the working electrode. Thus, if the working electrode is not completely perfect in function, the reliability of the reference electrode becomes poor. In the present invention, a correction electrode whose function is completely guaranteed is introduced for the prevention of this problem and the improvement in self-diagnostic function, making the reference electrode independent.

Therefore, in accordance with another embodiment, there is provided a potentiometric three-electrode system comprising a working electrode and a reference electrode supplemented with a correction electrode, in which the working electrode and the reference electrode are measured in potential as being relative to the correction electrode.

Figure 3:
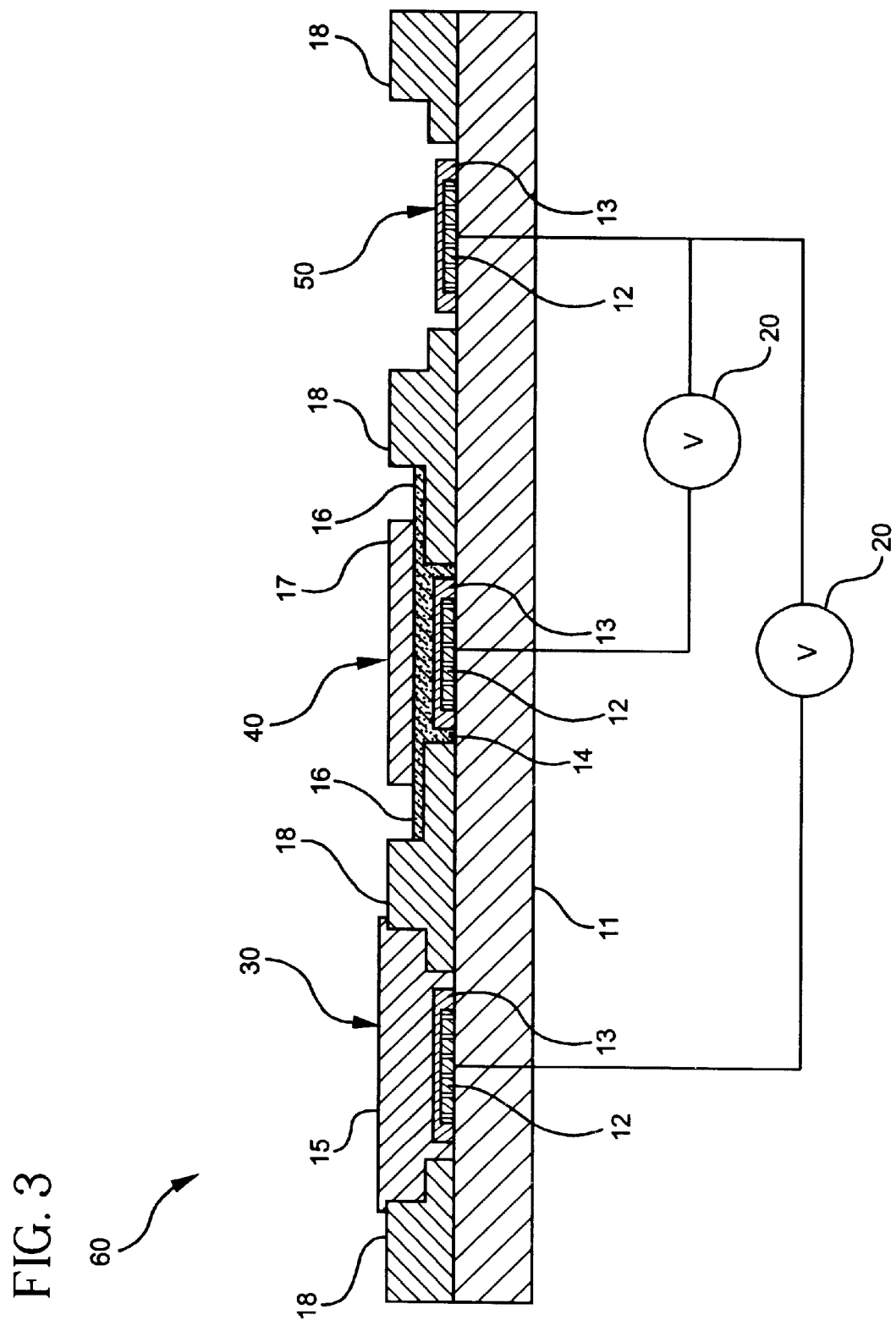
FIG. 3 as a schematic cross sectional view showing a potentiometric tri-electrode system consisting of a working electrode, a reference electrode and a correction electrode.

With reference to FIG. 3, there is shown the potentiometric tri-electrode system (working electrode 30, reference electrode 40 and correction electrode 50) of the present invention. The working electrode 30 and the reference electrode 40 are the same as in the potentiometric bi-electrode system of the present invention. The correction electrode 50 incorporates an insoluble metal salt 13 such as silver halides, guaranteeing perfect function for the corresponding halide ions. That is, silver chloride, silver bromide and silver iodide electrodes react perfectly with chloride ion, bromide ion, and iodide ion, respectively.

A better understanding of the present invention may be obtained in light of the following examples which are set forth to illustrate, but are not to be construed to limit the present invention.

EXAMPLE 1

Construction of Potentiometric Electrode System with Self-Diagnosis Function

A potentiometric bi-electrode system of the present invention was constructed as follows.

Polyvinylpyrrolidone was dissolved at an amount of 6 wt % in an aqueous 2M KCl solution to prepare an inner reference solution, In 1 ml of tetrahydrofuran, polyurethane was dissolved at an amount of 33 wt %, along with 1 wt % of valinomycin as a potassium ion-selective material and 66 wt % of bis(2-ethylhexyl) adipate as a plasticizer, to give an ion-selective, protective membrane.

A potassium ion-selective electrode membrane in the working electrode was prepared as the above ion-sensitive, protective membrane comprising the potassium ion-selective material.

The reference electrode thus prepared was measured or electrochemical properties, together with a conventional reference electrode.

EXAMPLE 2

Figure 4:
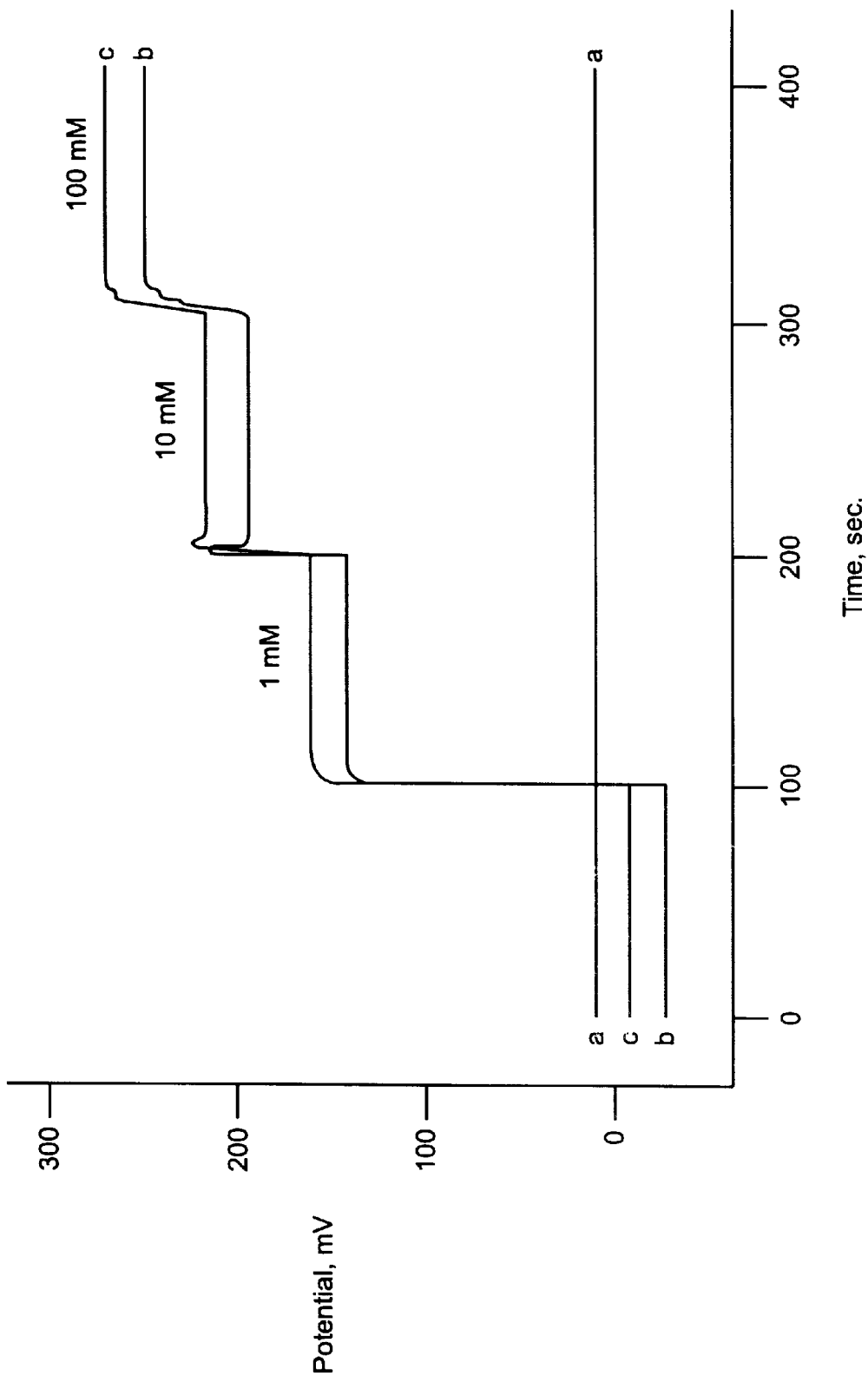
FIG. 4 is a graph showing the operational features of the potentiometric electrode system of the present invention by the reference electrode when the junction is not contaminated (a), by the reference electrode when the junction is contaminated (b), and by the working electrode provided with a potassium ion-selective electrode membrane (c)

Operational Features of Abnormality According to Junction Contamination of Reference Electrode With reference to FIG. 4, the operational features of the potentiometric electrode system of the present invention are shown by the reference electrode when the junction is not contaminated (a), by the reference electrode when the junction is contaminated (b), and by the working electrode provided with a potassium ion-selective electrode membrane (c). As shown in this potentiometric graph, when the junction is not contaminated, the reference electrode keeps its potential irrespective of the concentration change of potassium chloride. In contrast, junction contamination makes the reference electrode react with potassium ion in accordance with the concentration change of potassium chloride, exhibiting a similar feature to the reactivity of the working electrode provided with the potassium ion-selective electrode membrane. Thus, the electrode system into which the reference electrode of such a self-diagnosis function is introduced shows apparent abnormal reactivity when an abnormality occurs at the junction of the reference electrode. Therefore, the reference electrode can diagnose itself as its abnormality, thereby excluding the suspicion that the measured values might not be reliable because the junction contamination cannot be accurately examined in conventional reference electrodes.

EXAMPLE 3

Activation Time of Reference Electrode According to Junction Area

Figure 5:
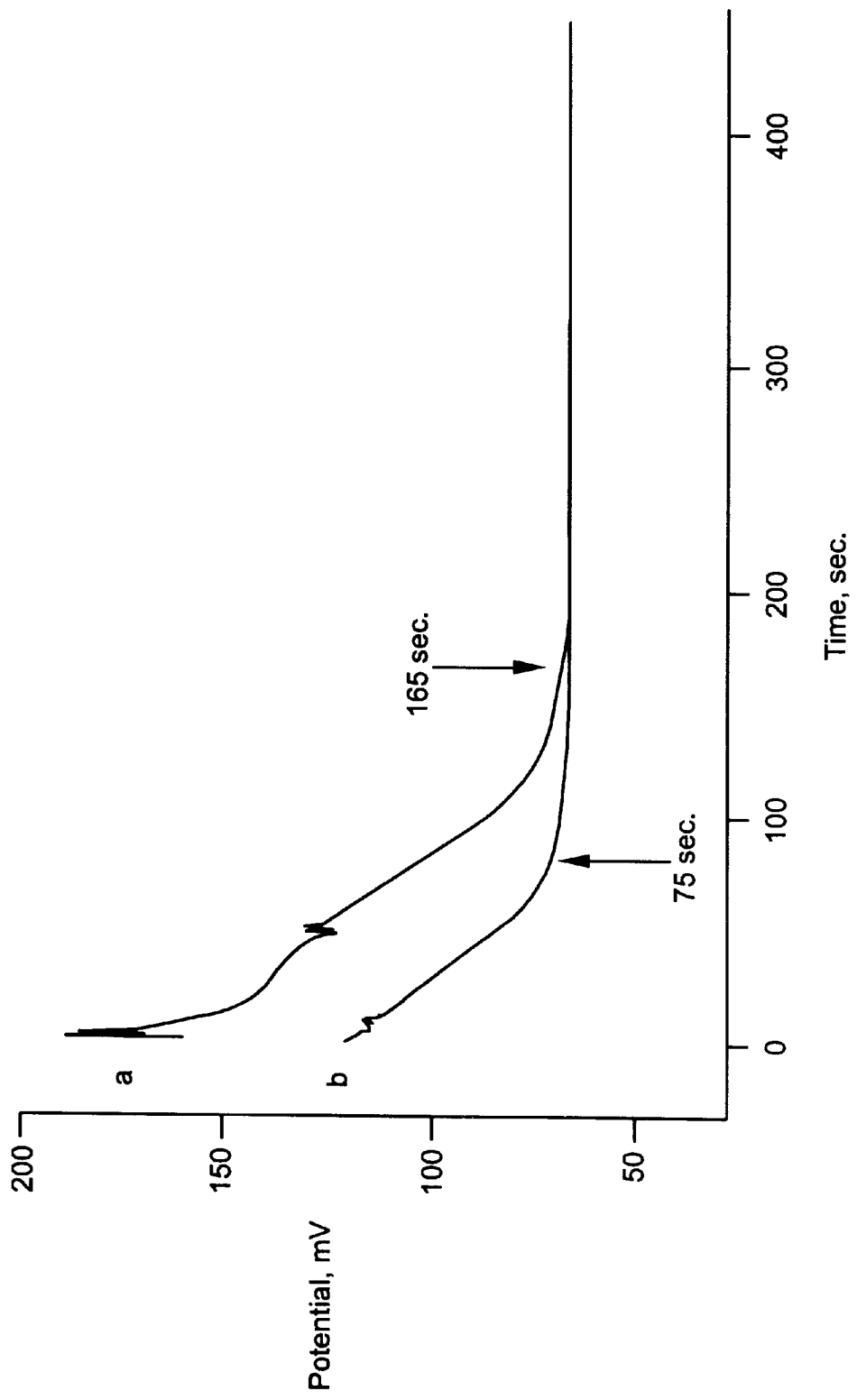
FIG. 5 is a graph comparing the activation times of reference electrodes between when a single junction (a) is formed and when a double junction (b) is formed.

With reference to FIG. 5, the activation times of reference electrodes are compared between when a single junction (a)

is formed and when a double junction (b) is formed. As shown in tho graph, it takes about 165 sec for the electrode with a single junction (a) to be activated, while the reference junction with a double junction needs only 75 sec for its activation, which is twice as fast as the activation of the reference electrode of the relatively small junction area. The activation time was determined as the time period it took to firstly meet a potential flow of 0.2 mV or less per min required for clinical examination.

EXAMPLE 4

Figure 6A:
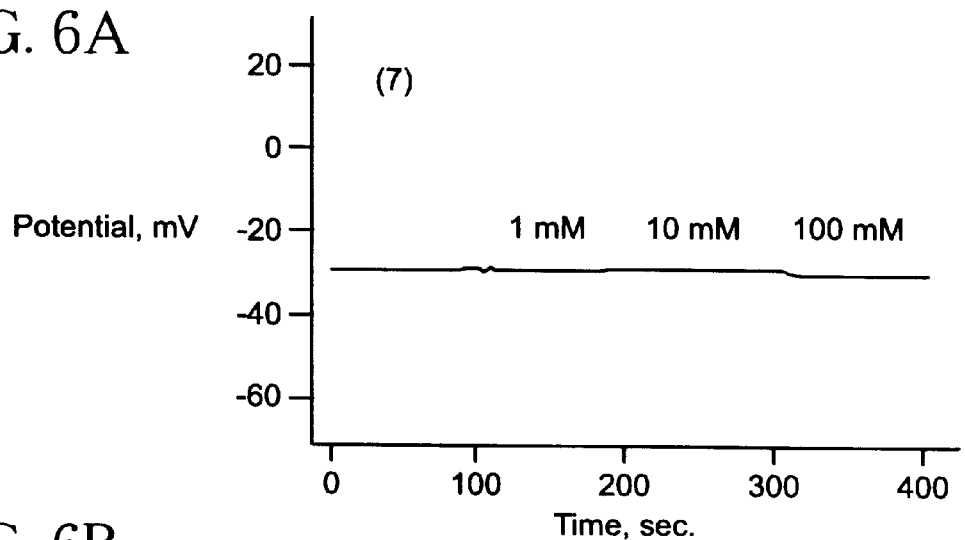
FIG. 6 is a graph showing the stability of the reference electrode of the present invention to clinically important ions within blood: to potassium ion and chloride ion (a); sodium ion and chloride ion (b); and to calcium ion and chloride ion (c)
Figure 6B:
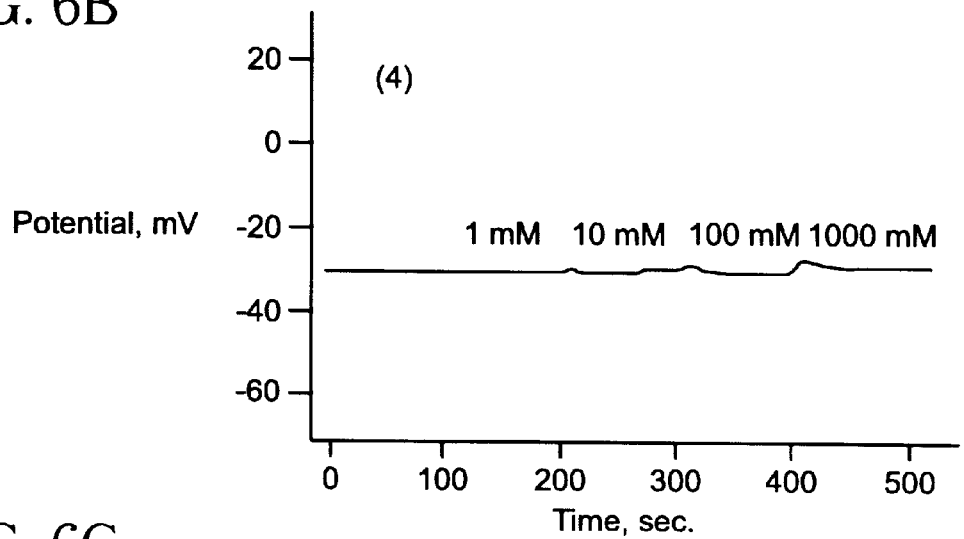
Figure 6C:
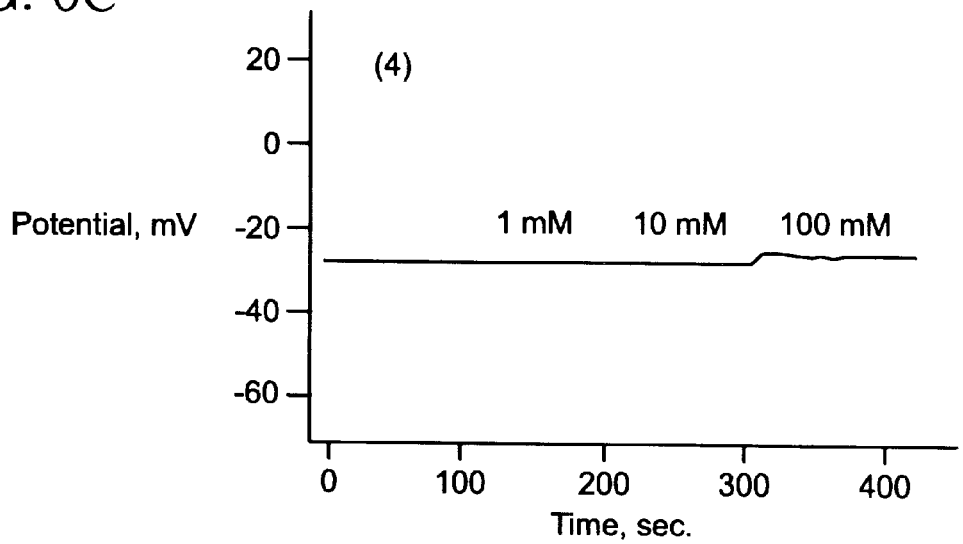

Stability of Reference Electrode (1) Stability to Clinically Important Ion Species within Blood With reference to FIG. 6, there is shown the stability of the reference electrode of the present invention to clinically important ions within blood: to potassium ion and chloride ion (a); sodium ion and chloride ion (b); and to calcium ion and chloride ion (c). As shown in these graphs, the reference electrode of the present invention maintains stable potentials even at concentrations several tens of times as high as the clinically normal concentrations (potassium ion: 3.6–5.0 mM, sodium ion 135–145 mM, calcium ion: 1.14–1.31 mM, chloride ion: 101–111 mM) and thus, can perform its own full function.

(2) Stability to pH

Figure 7:
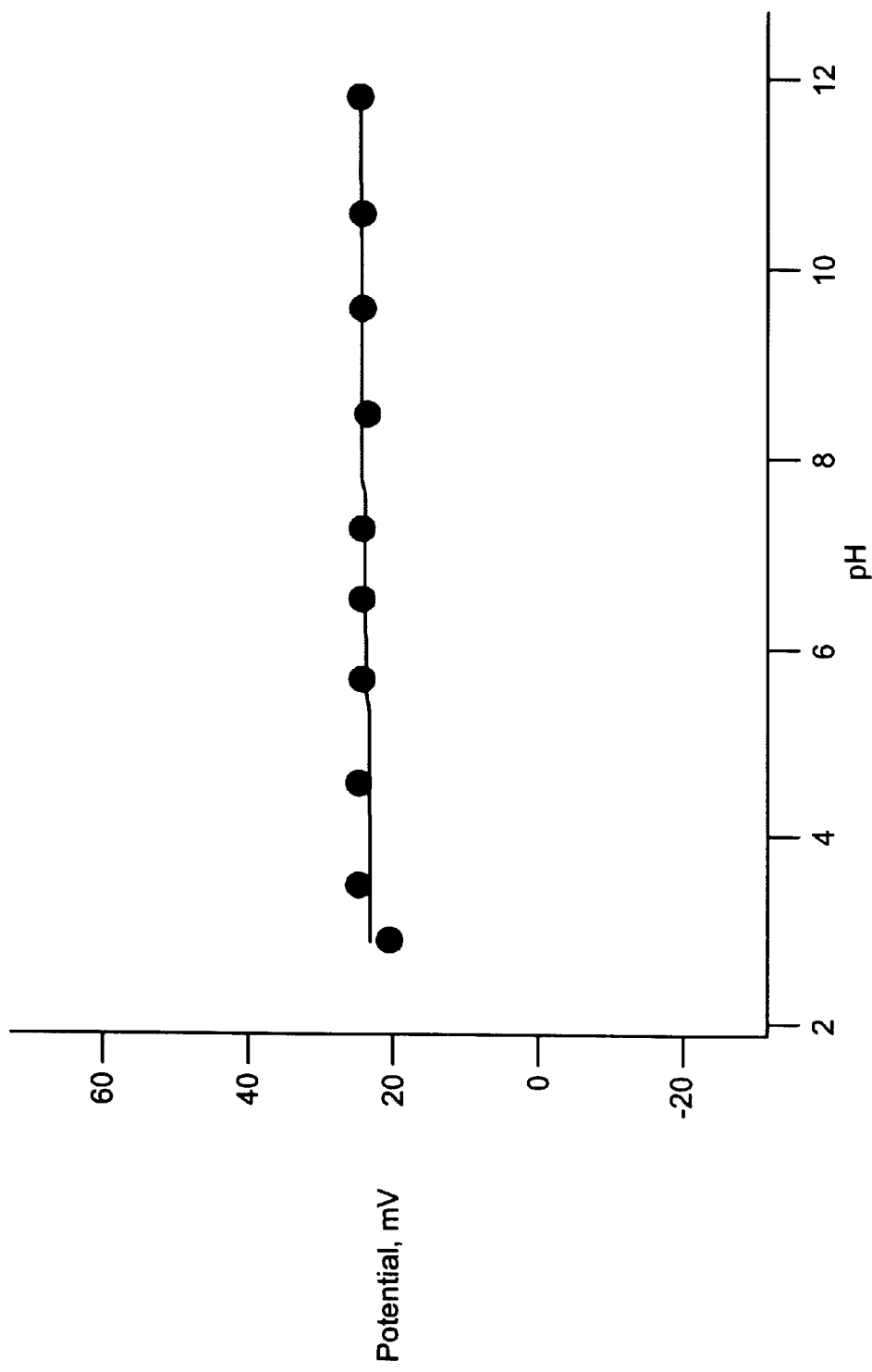
FIG. 7 is a graph showing the stability of the reference electrode of the present invention to pH change.

With reference to FIG. 7, the reference electrode shows a potential slope of 0.15 mM/pH over a pH range of 3–12 (clinically normal pH 7.35–7.45), remaining almost unchanged in potential.

(3) Stability to Concentration Change of Mixed Ions

Figure 8:
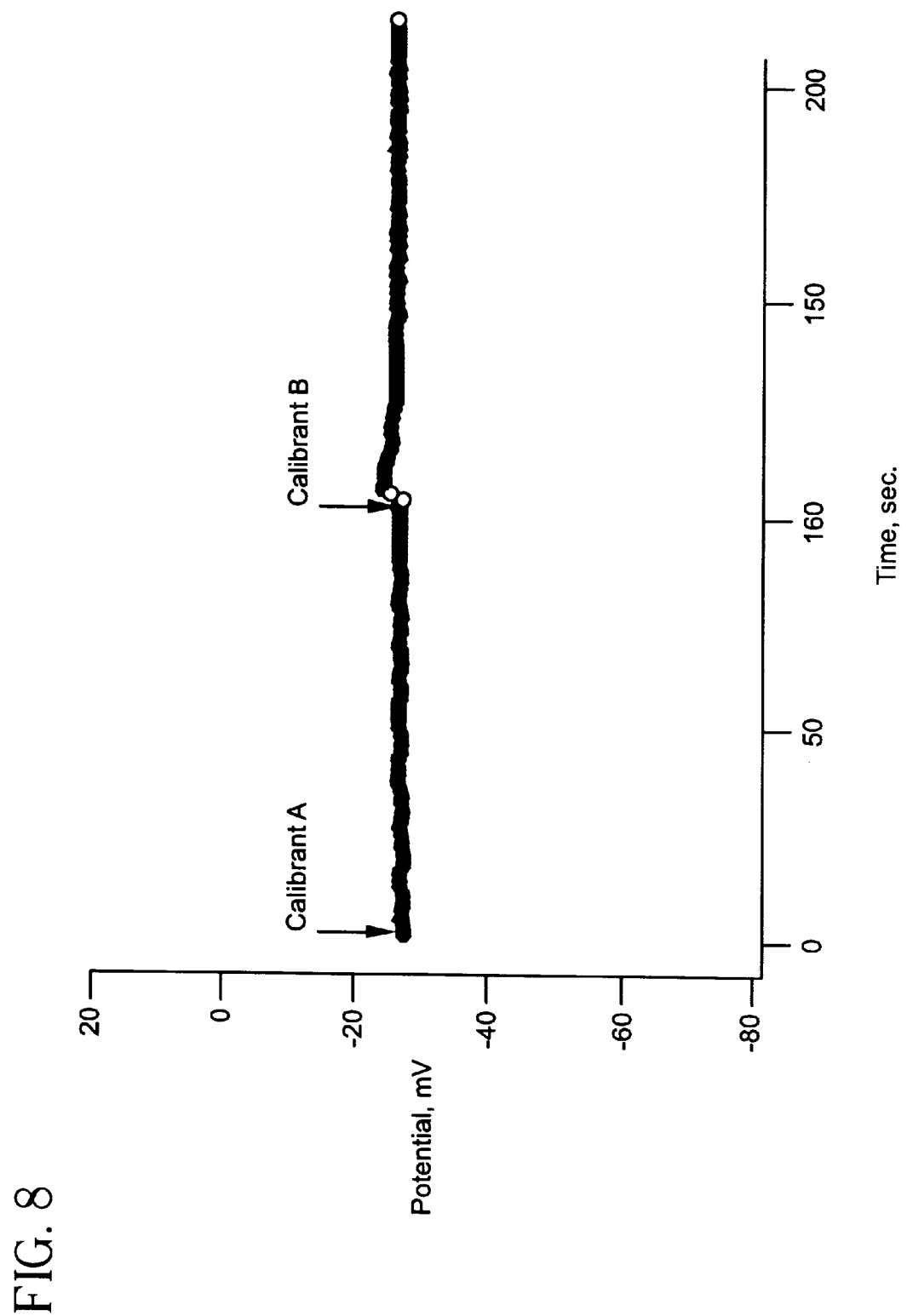
FIG. 8 is a graph showing the stability of the reference electrode of the present invention to the concentration change of mixed ions.

With reference to FIG. 8, a potential change of the reference electrode is plotted against a concentration change of mixed ions over a period of time. To make a concentration change of mixed ions, a clinical calibrant A (1 mM potassium ion, 150 mM sodium ion, 1 mM calcium ion, 120 mM chloride ion, pH 7.4) was used, followed by the addition of a clinical calibrant B (10 mM potassium ion, 50 mM sodium ion, 5 mM calcium ion, 50 mM chloride ion, pH 6.8). As shown in the graph, the reference electrode kept its potential constant against the concentration change of mixed ionic species.

The data obtained in the above Examples demonstrate that the reference electrode employing the ion-sensitive, protective membrane of the present invention is superior in self-diagnosis function and potential stability as well as activation within a short time period.

As described hereinbefore, the present invention provides a miniaturized solid-state reference electrode that includes an ion-selective membrane containing an ion-sensing materials as a protective membrane for the inner reference solution to diagnose by itself an operational abnormality such as junction contamination as well as employing a double junction so as to perform its own full function, even when one junction is contaminated, by virtue of the other junction. In addition, the solid-state reference electrode enjoys the advantage of reaching activation within a short period of time because of being able to absorb moisture from samples through its open two junctions.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A reference electrode for a potentiostatic electrode system, comprising:
   a substrate;
   a metal layer;
   an insoluble metal salt layer;
   an insulating film for insulating the metal layer from a sample solution;
   a hydrogel serving as an inner reference solution; and
   an ion sensitive, protective membrane containing an ion selective material, the ion sensitive, protective membrane being formed on only a portion of the hydrogel such that at least two portions of the hydrogel are not covered by the ion-sensitive, protective membrane and thereby form a plurality of junctions, the ion-sensitive, protective membrane being arranged to separate the inner reference solution from the sample solution and act as an ion-sensing membrane upon contamination of the junctions.

2. The reference electrode as set forth in claim 1, wherein the substrate is prepared from plastic or ceramic, the metal layer is prepared from a pure metal or an alloy, the insoluble metal salt layer is prepared from a silver halide, the insulating film is prepared from a non-conductive polymer, the hydrogel is prepared from a water-soluble polymer saturated with a salt, and the ion-sensitive, protective membrane is prepared from an ion-selective electrode membrane.

3. The reference electrode as set forth in claim 2, wherein the substrate is made of poly(vinyl chloride) or alumina ($Al_2O_3$); the metal layer is made of a metal selected from the group consisting of silver (Ag), platinum (Pt), gold (Au), copper (Cu) and alloys thereof; the insoluble metal salt layer is made of a silver halide selected from the group consisting of silver chloride (AgCl), silver bromide (AgBr) and silver iodide (AgI); the insulating film is a ceramic film, a dielectric film or a photosensitive film; the hydrogel is prepared by dissolving a water-soluble compound selected from the group consisting of polyacrylic acid, METHOCEL® (methylated cellulose), polyvinylalcohol, (hydroxypropyl) methyl cellulose, polyvinylpyrrolidone, poly(methyl methacrylate), agar and gelatin at 0.5–30 wt % in a saturated solution of KCl, $KNO_3$, or $NH_4NO_3$ in water; and the ion-sensitive, protective membrane is selected from the group consisting of a potassium ion-, a sodium ion-, a calcium ion- and a chloride ion-selective electrode membrane.

4. The reference electrode as set forth in claim 3, wherein the ion-sensitive, protective membrane has a polymer support selected from the group consisting of poly(vinyl chloride), silicone rubber and polyurethane.

5. The reference electrode as set forth in claim 1 further comprising a correction electrode for more accurate self-diagnostic function.

6. The reference electrode as set forth in claim 5, wherein the correction electrode comprises a substrate; a metal layer; an insoluble metal salt layer; and an insulating film for insulating the metal layer from a sample solution.

7. The reference electrode as set forth in claim 6, wherein the substrate of the correction electrode is prepared from plastic or ceramic, the metal layer of the correction electrode is prepared from a pure metal or an alloy, the insoluble metal salt layer of the correction electrode is prepared from a silver halide, and the insulating film of the correction electrode is prepared from an inorganic or an organic polymer.

8. The reference electrode as set forth in claim 7, wherein the substrate of the correction electrode is made of poly(vinyl chloride) or alumina ($Al_2O_3$); the metal layer of the correction electrode is made of a metal selected from the group consisting of silver (Ag), platinum (Pt), gold (Au), copper (Cu) and alloys thereof; the insoluble metal salt layer of the correction electrode is made of a silver halide selected from the group consisting of silver chloride (AgCl), silver bromide (AgBr) and silver iodide (AgI); and the insulating film of the correction electrode is a ceramic film, a dielectric film or a photosensitive film.

9. The reference electrode as set forth in claim 5, wherein the correction electrode comprises a metal layer and an insoluble metal salt layer.

10. The reference electrode as set forth in claim 1, wherein the substrate is planar.

11. The reference electrode as set forth in claim 1, further comprising a working electrode formed on the substrate.

12. The reference electrode as set forth in claim 11, wherein the working electrode comprises a metal layer, an insoluble metal salt layer, an ion-selective membrane, the insulating film surrounding the ion-selective membrane.

13. The reference electrode as set forth in claim 11, further comprising a correction electrode formed on the substrate.

14. The reference electrode as set forth in claim 13, wherein the correction electrode comprises a metal layer and an insoluble metal salt layer.

15. The reference electrode as set forth in claim 1, wherein the ion-sensitive, protective membrane is selected from the group consisting of a potassium ion-, a sodium ion-, a calcium ion- and a chloride ion-selective electrode membrane.

16. The reference electrode as set forth in claim 1, wherein the ion-sensitive, protective membrane has a polymer support selected from the group consisting of poly(vinyl chloride), silicone rubber and polyurethane.

17. The reference electrode as set forth in claim 1, wherein the plurality of junctions consist of two junctions formed on opposite sides of the ion-sensitive, protective membrane.

* * * * *